United States Patent
Okada et al.

(10) Patent No.: US 8,425,990 B2
(45) Date of Patent: Apr. 23, 2013

(54) LIQUID CRYSTALLINE COMPOUND, LIQUID CRYSTALLINE COMPOSITION, OPTICAL FILM, AND OPTICAL LAMINATE

(75) Inventors: Seiji Okada, Tokyo (JP); Kentarou Tamura, Tokyo (JP)

(73) Assignee: Zeon Corporation, Tokyo (JP)

( * ) Notice: Subject to any disclaimer, the term of this patent is extended or adjusted under 35 U.S.C. 154(b) by 777 days.

(21) Appl. No.: 12/526,119

(22) PCT Filed: Feb. 21, 2008

(86) PCT No.: PCT/JP2008/052937
§ 371 (c)(1),
(2), (4) Date: Dec. 14, 2009

(87) PCT Pub. No.: WO2008/102838
PCT Pub. Date: Aug. 28, 2008

(65) Prior Publication Data
US 2010/0119737 A1 May 13, 2010

(30) Foreign Application Priority Data
Feb. 23, 2007 (JP) ................................ 2007-044425

(51) Int. Cl.
*C09K 19/00* (2006.01)
(52) U.S. Cl.
USPC .................. 428/1.3; 252/299.01; 252/299.64; 349/86; 349/117; 544/224; 544/298; 564/313
(58) Field of Classification Search .................. 428/1.1, 428/1.3; 349/1, 86, 117; 430/20; 252/299.01, 252/299.6, 299.61, 299.63, 299.66, 299.68, 252/299.64; 544/224, 298; 546/341, 339; 549/369, 370; 564/313
See application file for complete search history.

(56) References Cited

U.S. PATENT DOCUMENTS

| | | | |
|---|---|---|---|
| 4,385,067 A | 5/1983 | Resnick | |
| 2003/0072893 A1* | 4/2003 | Nakano et al. ................. | 428/1.1 |
| 2009/0117292 A1 | 5/2009 | Tamura | |

FOREIGN PATENT DOCUMENTS

| | | |
|---|---|---|
| JP | 10-147562 | 6/1998 |
| JP | 2001-220583 A1 | 8/2001 |
| JP | 2002-265421 A1 | 9/2002 |
| WO | WO 2007/142206 A1 | 12/2007 |

OTHER PUBLICATIONS

Makoto, Negishi, et al. "Development of Liquid Crystalline Azines for STN-LCD," DIO Technical Review, No. 5, 1999, pp. 17-20 (with its English translation).
M. Negishi, et al.; "Development of Liquid Crystalline Azines for STN-LCD;" DIC Technical Review; 1999; vol. 5; pp. 17-20 (4 Sheets total.).
International Search Report for International Application No. PCT/JP2008/052937 dated Mar. 12, 2008.

\* cited by examiner

*Primary Examiner* — Angela Ortiz
*Assistant Examiner* — Ruiyun Zhang
(74) *Attorney, Agent, or Firm* — Kratz, Quintos & Hanson, LLP

(57) ABSTRACT

A liquid crystalline compound shown by the following formula (I).

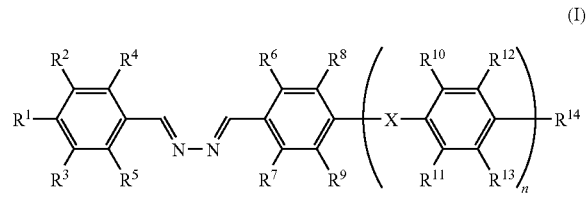

wherein $R^1$ to $R^{13}$ represent a hydrogen atom, a fluorine atom, a methyl group, a trifluoromethoxy group, or a cyano group, X represents —O—, —O—CO—, or the like, n is 0 or 1, and $R^{14}$ represents -A-CO—CH=$CH_2$, wherein A is a linking group. The liquid crystalline compound has a higher liquid crystal phase upper limit temperature, is chemically stable, can be inexpensively produced, and exhibits a large selective reflection wavelength zone Δλ (a large Δn). A liquid crystalline composition comprising the liquid crystalline compounds, an optical film having a liquid crystal layer formed using the liquid crystalline composition, and an optical laminate comprising a substrate, an alignment film formed on the substrate, a liquid crystal layer formed using the liquid crystalline composition on the alignment film are also disclosed.

13 Claims, No Drawings

LIQUID CRYSTALLINE COMPOUND, LIQUID CRYSTALLINE COMPOSITION, OPTICAL FILM, AND OPTICAL LAMINATE

TECHNICAL FIELD

The present invention relates to a liquid crystalline compound suitable for producing an organoelectronic material and an intermediate of medical and agricultural chemicals, particularly a liquid crystal material for electrooptical liquid crystal displays, a liquid crystalline composition using the liquid crystalline compound, and an optical film and an optical laminate having a liquid crystal layer formed from the composition.

BACKGROUND ART

In recent years, a liquid crystal alignment film produced by an orientation treatment of a liquid crystal polymer or a liquid crystalline compound having a polymerizable functional group has been developed as an optical film for an optical compensator and the like used for a liquid crystal display. This film attracts attention as being capable of providing a high degree of orientation, i.e. oblique orientation, torsion orientation, and the like, which cannot be obtained by a birefringence film utilizing the polymer film stretching technology.

A cholesteric polarizer utilizing selective reflection characteristics of a liquid crystal alignment film (selective reflection film) obtained by cholesteric orientation of a compound comprising a liquid crystal polymer or a polymerizable liquid crystal compound such as a liquid crystalline (meth)acrylate compound and a chiral compound has also been put on practical use.

The selective reflection center wavelength ($\lambda$) which is one of the selective reflection characteristics is shown by the formula $\lambda = n \times P$ (wherein n is the average refractive index and P is a cholesteric pitch). The selective reflection wavelength zone ($\Delta\lambda$) is shown by the formula $\Delta\lambda = \Delta n \times P$ (wherein $\Delta n$ is (ne−no), wherein ne indicates an extraordinary light refractive index and no indicates an ordinary light refractive index). Therefore, in order to expand the selective reflection wavelength zone ($\Delta\lambda$), a material having a large $\Delta n$ is desired.

In order to use a selective reflection film as a cholesteric polarizer for a liquid crystal display, the film must exhibit selective reflection in the visible ray region. Since the selective reflection wavelength zone $\Delta\lambda$ in one layer of a selective reflection film is usually narrower than a visible ray region, two or more selective reflection films are laminated in order to broaden the selective reflection wavelength zone $\Delta\lambda$. For this reason, the selective reflection film using a material having a narrow selective reflection wavelength zone $\Delta\lambda$ requires a large number of layers of lamination, resulting in low productivity. Therefore, a material (such as a polymerizable liquid crystal compound) having a large $\Delta n$, that is, a material having a wide selective reflection wavelength zone $\Delta\lambda$, has been desired.

However, generally known polymerizable compounds having a large $\Delta n$ exhibits poor solubility, applicability, and orientation properties. Some of them cannot produce a uniform film and have difficulty in providing a usable selective reflection film.

Azines shown by the following formula (A) have been known for many years and used as liquid crystalline compounds.

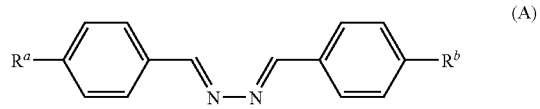

(A)

wherein $R^a$ represents an alkyl group and $R^b$ represents an alkyl group, a cyano group, a fluorine atom, a trifluoromethoxy group, or the like.

These compounds are liquid crystalline materials having excellent properties such as a high liquid crystal phase upper limit temperature and being comparatively chemically stable and inexpensively produced.

However, these azines are not necessarily satisfactory as to mutual solubility with general purpose liquid crystal compounds used at the present time. Although the mutual solubility can be improved to a certain extent by increasing the number of carbon atoms in the side chain alkyl group in the formula (A), such a compound has a low liquid crystal phase upper limit temperature.

In order to solve such a problem, a liquid crystalline compound shown by the following formula (B) has been proposed in Patent Document 1.

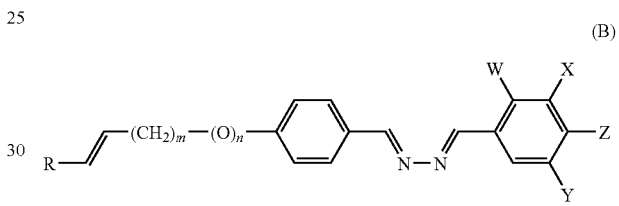

(B)

wherein R is a hydrogen atom or an alkyl group having 1 to 12 carbon atoms, the double bond is in a trans displacement when R is an alkyl group, m represents an integer of 1 to 10, n is 0 or 1, W, X, and Y individually represent a fluorine atom, a chlorine atom, a methyl group, a cyano group, or a hydrogen atom, and Z represents a fluorine atom, a chlorine atom, a cyano group, an alkyl or alkoxyl group having 1 to 12 carbon atoms, or an alkenyl or alkenyloxy group having 3 to 12 carbon atoms, wherein one or more hydrogen atoms in these groups may be substituted with fluorine atoms.

These compounds are chemically stable to heat, light, and the like, have excellent liquid crystallinity, and can be easily manufactured industrially. Since the compounds have excellent mutual solubility with general liquid crystalline compounds and crystalline compositions, the crystal response time can be significantly improved by using the compounds. Therefore, the compounds are usable as components of a liquid crystalline material for a liquid crystal display element having a wide temperature range and being capable of responding promptly.

However, performance of liquid crystal display devices is advancing day by day in recent years, demanding development of a liquid crystalline material having a higher liquid crystal phase upper limit temperature, which is chemically stable, can be inexpensively produced, and exhibits a large $\Delta n$.

Patent Document 1: JP-A-10-147562 (U.S. Pat. No. 6,010,642)

DISCLOSURE OF THE INVENTION

Problems to be Solved by the Invention

The present invention has been achieved in view of the above-mentioned problems in general technologies and has an object of providing a liquid crystalline compound having a higher liquid crystal phase upper limit temperature, which is chemically stable, can be produced inexpensively, and exhibits a large selective reflection wavelength zone Δλ (a large Δn), a liquid crystalline composition containing this compound, and an optical film and an optical laminate having a liquid crystal layer formed from the composition.

Means for Solving the Problems

In order to achieve the above object, the inventors of the present invention have conducted extensive studies and have synthesized a compound shown by the following formula (I*).

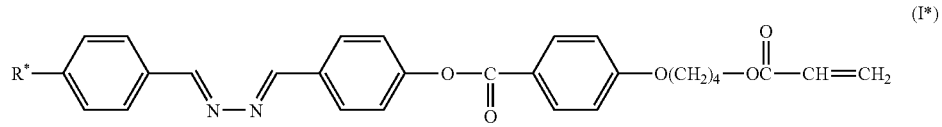

wherein R* represents a hydrogen atom, a fluorine atom, a trifluoromethyl group, a cyano group, or the like.

The inventors have found that these compounds are chemically stable to heat, light, and the like, have excellent liquid crystallinity, can be easily manufactured industrially, exhibit a large selective reflection wavelength zone Δλ (that is, a large Δn), and is useful as a material for forming a cholesteric liquid crystal layer. This finding has led to the completion of the present invention.

Accordingly, a first aspect of the present invention of the present application provides a liquid crystalline compound shown by the following formula (I):

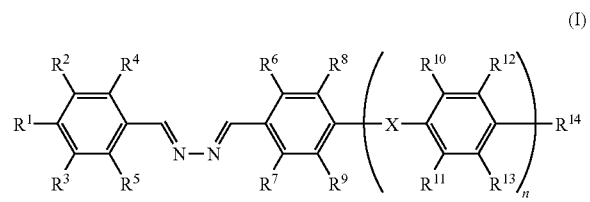

wherein $R^1$ to $R^{13}$ individually represent a hydrogen atom, a halogen atom, an alkyl group having 1 to 6 carbon atoms, an alkoxy group having 1 to 6 carbon atoms, a haloalkyl group having 1 to 6 carbon atoms, a haloalkoxy group having 1 to 6 carbon atoms, an alkenyl group having 2 to 6 carbon atoms, an alkenyloxy group having 2 to 6 carbon atoms, a cyano group, or a thiocyanate group; X represents —O—, —O—CO—, or —CO—O—; n is 0 or 1; and $R^{14}$ represents a group shown by the formula -A-CO—$CR^{15}$=$CH_2$, wherein $R^{15}$ represents a hydrogen atom or an alkyl group having 1 to 6 carbon atoms, and A represents a linking group. —CO— in the above and other formulas represents a carbonyl group.

A second aspect of the present invention provides a liquid crystalline composition comprising one or more liquid crystalline compounds of the present invention.

The liquid crystalline composition of the present invention preferably comprises (a) a liquid crystalline compound of the present invention and a polyfunctional (meth)acrylate compound having two or more groups shown by the formula —O—CO—$CR^{16}$=$CH_2$, wherein $R^{16}$ represents a hydrogen atom or a methyl group in the molecule, or (b) a liquid crystalline compound of the present invention and a chiral compound, and more preferably a liquid crystalline compound of the present invention, a polyfunctional (meth)acrylate compound, and a chiral compound.

A third aspect of the present invention provides an optical film having a liquid crystal layer formed using the liquid crystalline composition of the present invention.

A fourth aspect of the present invention provides an optical laminate comprising a substrate, an alignment film formed on the substrate, and a liquid crystal layer formed on the alignment film using the liquid crystalline composition of the present invention.

Effects of the Invention

The liquid crystalline compound and the liquid crystalline composition of the present invention are liquid crystalline materials having a high liquid crystal phase upper limit temperature, that are chemically stable, manufactured at a low cost, and exhibit a large selective reflection wavelength zone Δλ (that is, a large Δn).

When a chiral compound is contained, the liquid crystalline composition of the present invention has a high liquid crystal phase upper limit temperature and can form a liquid crystal layer having a large selective reflection wavelength zone Δλ (that is, a large Δn).

The optical film and the optical laminate of the present invention are inexpensive and have a high quality due to the possession of the liquid crystal layer formed using the liquid crystalline composition of the present invention.

BEST MODE FOR CARRYING OUT THE INVENTION

The present invention will be described in detail for each of the items of 1) a liquid crystalline compound, 2) a liquid crystalline composition, 3) an optical film, and 4) an optical laminate.

1) Liquid Crystalline Compound

The liquid crystalline compound of the present invention is a compound shown by the above formula (I).

In the formula (I), $R^1$ to $R^{13}$ individually represent a hydrogen atom; a halogen atom such as a fluorine atom, a chlorine atom, and a bromine atom; an alkyl group having 1 to 6 carbon atoms such as a methyl group, an ethyl group, a propyl group, and an isopropyl group; an alkoxy group having 1 to 6 carbon atoms such as a methoxy group, an ethoxy group, a propoxy group, and an isopropoxy group; a haloalkyl group having 1 to 6 carbon atoms such as a fluoromethyl group, a chloromethyl group, a difluoromethyl group, a dichloromethyl group, a trifluoromethyl group, and a trichloromethyl group; a haloalkoxy group having 1 to 6 carbon atoms such as a fluoromethoxy group, a chloromethoxy group, a difluoromethoxy group, a dichloromethoxy group, a trifluoromethoxy group, and a pentafluoroethoxy group; an alkenyl group having 2 to 6 carbon atoms such as a vinyl group and an allyl group; an alkenyloxy group having 2 to 6 carbon atoms such as an allyloxy group; a cyano group; or a thiocyanate group.

In the liquid crystalline compound, it is preferable that $R^1$ to $R^3$ individually represent a hydrogen atom, a halogen atom, an alkyl group having 1 to 6 carbon atoms, an alkoxy group having 1 to 6 carbon atoms, a haloalkyl group having 1 to 6 carbon atoms, a haloalkoxy group having 1 to 6 carbon atoms, or a cyano group, and it is more preferable that $R^1$ to $R^3$ individually represent a hydrogen atom, a halogen atom, an alkyl group having 1 to 6 carbon atoms, a haloalkoxy group having 1 to 6 carbon atoms, or a cyano group, and $R^4$ to $R^{13}$ individually represent a hydrogen atom, an alkyl group having 1 to 6 carbon atoms, an alkoxy group having 1 to 6 carbon atoms, or a haloalkyl group having 1 to 6 carbon atoms, from the viewpoint of availability.

X represents —O—, —O—CO—, or —CO—O— and n is 0 or 1.

$R^{14}$ represents a group shown by the formula -A-CO—$CR^{15}$=$CH_2$, wherein $R^{15}$ represents a hydrogen atom or an alkyl group having 1 to 6 carbon atoms.

A represents a linking group. The term "linking group" refers to a single bond or a divalent group. There are no specific limitations to the linking group represented by A insofar as the group links a benzene ring with a group shown by the formula —C(=O)—C($R^{15}$)=$CH_2$.

Groups shown by —O—, —CO—O—$(CHR^{17})_a$—O—, —O—CO—O—$(CHR^{18})_b$—O—, —O—$(CHR^{19})_c$—O—, or —O—$(CH_2CHR^{20}O)_d$— are preferable as A.

In the above formulas, $R^{17}$ to $R^{20}$ individually represent a hydrogen atom or a methyl group and a, b, c, and d show optional natural numbers. When a, b, c, or d is 2 or more, the groups shown by —$CHR^{17}$—, the groups shown by —$CHR^{18}$—, the groups shown by —$CHR^{19}$—, and the groups shown by —$CH_2CHR^{20}O$— may be respectively either the same or different. a, b, c, and d are preferably integers of 1 to 10.

Among these, —O—$(CHR^{19})_c$—O— is preferable as A, with —O—$(CH_2)_c$—O— being more preferable, and —O—$(CH_2)_4$—O— being particularly preferable.

In the present invention, the compound shown by the above formula (I) is preferably a compound shown the following formula (Ia),

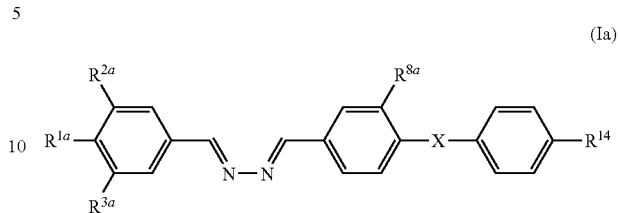

(Ia)

wherein $R^{1a}$ to $R^{3a}$ individually represent a hydrogen atom, a halogen atom, an alkyl group having 1 to 6 carbon atoms, an alkoxy group having 1 to 6 carbon atoms, a haloalkyl group having 1 to 6 carbon atoms, a haloalkoxy group having 1 to 6 carbon atoms, an alkenyl group having 2 to 6 carbon atoms, an alkenyloxy group having 2 to 6 carbon atoms, or a cyano group, $R^{8a}$ represents a hydrogen atom or an alkyl group having 1 to 6 carbon atoms, and $R^{14}$ and X are the same as defined above, and more preferably a compound shown by the following formula (Ib),

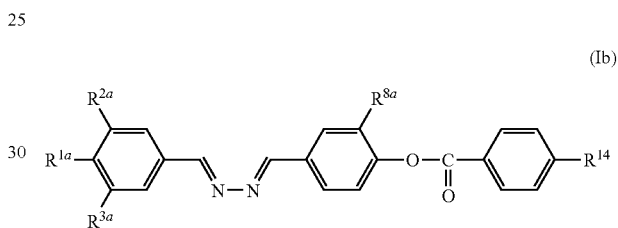

(Ib)

wherein $R^{1a}$ to $R^{3a}$, $R^{8a}$, and $R^{14}$ have the same meanings as defined above.

Specific examples of the compounds shown by the formula (I) including preferred compounds shown by the formula (Ib) are given below. In the following specific examples, —O—CO—$(CH_2)_2$—CO—O—$(CH_2)_2$—O— corresponds to the above-mentioned "divalent group".

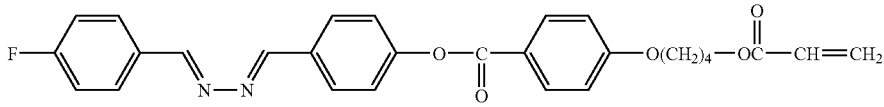

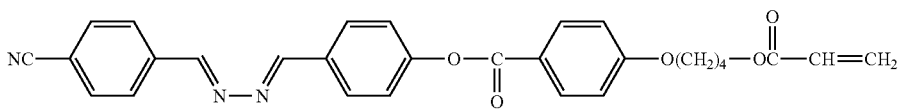

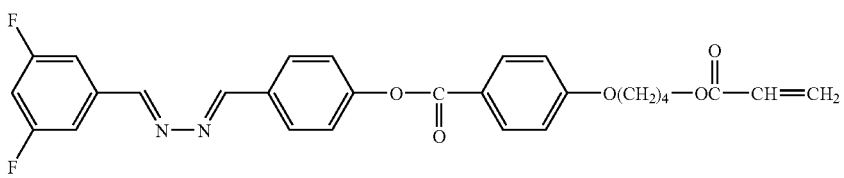

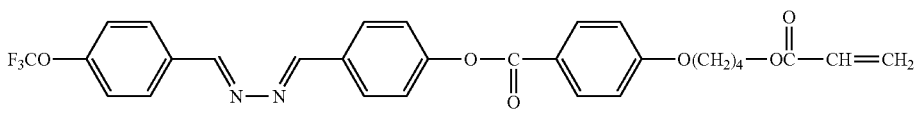

-continued
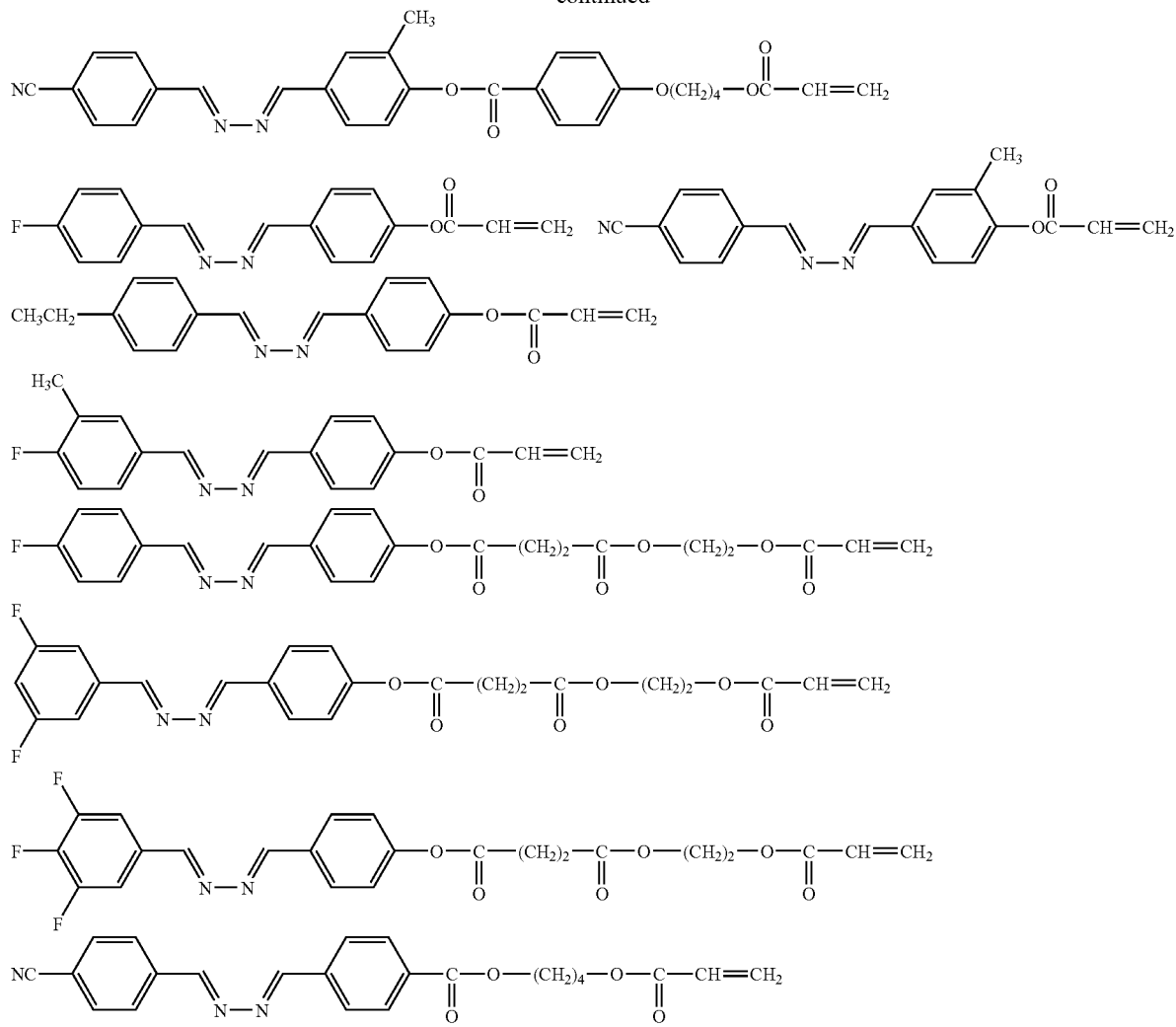
(Manufacturing Method)
The liquid crystalline compound of the present invention can be produced as follows, for example.
(Manufacturing Method 1)
Among the liquid crystalline compounds of the present invention, the compound (Ic) which is a compound having n=1 and X=—O—CO— in the above formula (I) can be manufactured as follows:
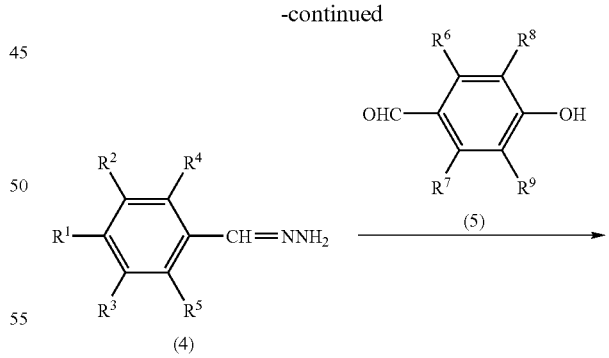
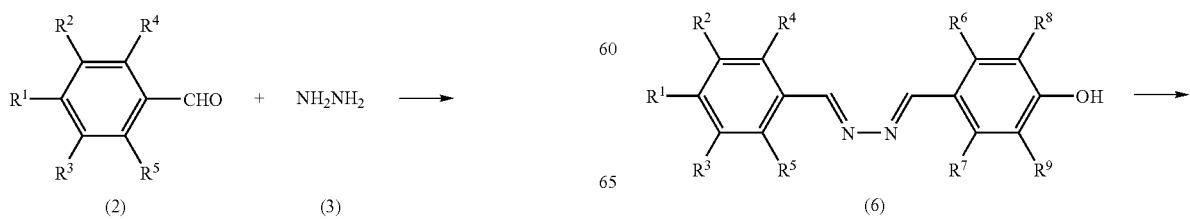

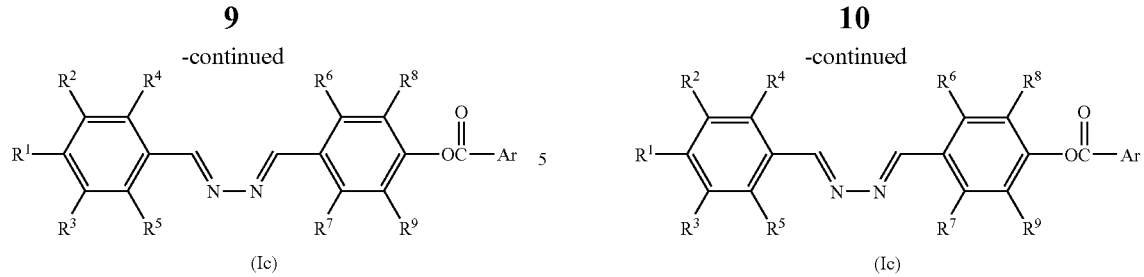

(Ic)

wherein $R^1$ to $R^9$ have the same meanings as defined above and Ar shows a substituted phenyl group indicated by the formula (C).

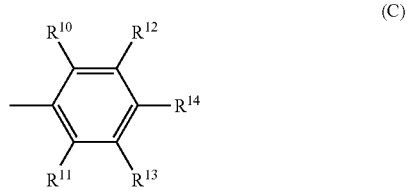

(C)

wherein $R^{10}$ to $R^{14}$ have the same meanings as defined above.

Specifically, first hydrazine (3) is reacted with a benzaldehyde compound shown by the formula (2) to obtain a hydrazone compound of the formula (4), which is reacted with a 4-hydroxybenzaldehyde compound of the formula (5) to obtain an N,N'-hydrazone compound shown by the formula (6).

The reaction to obtain a hydrazone compound of the formula (4) by reacting the hydrazine (3) with the benzaldehyde compound shown by the formula (2) is carried out in an appropriate organic solvent at a temperature in a range from room temperature to the boiling point of the solvent.

Although either anhydrous hydrazine or hydrazine hydrate may be used as the hydrazine (3), hydrazine hydrate is preferred in view of ease of handling. The amount of hydrazine used is usually 0.5 to 2 mols, preferably 0.8 to 1.2 mols per one mol of the benzaldehyde compound shown by the formula (2).

Examples of the organic solvent include alcohol solvents such as methanol, ethanol, propanol, and isopropanol; ether solvents such as diethyl ether, tetrahydrofuran, dioxane, and 1,2-dimethoxyethane; and aromatic hydrocarbon solvents such as benzene, toluene, and xylene.

The target compound (Ic) of the present invention can be obtained from the resulting product by any one of the following methods 1 to 3.

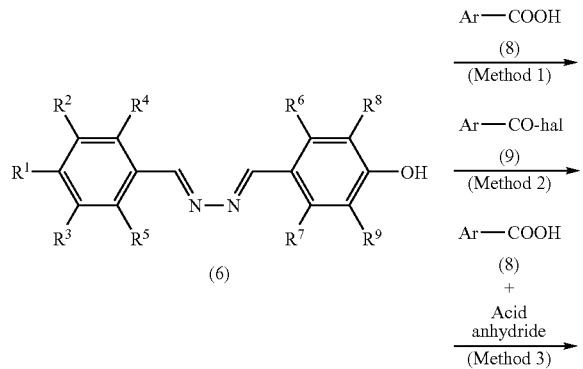

wherein $R^1$ to $R^9$ and Ar have the same meanings as defined above, and hal indicates a halogen atom.

(α) Method 1

The compound of the present invention shown by the formula (Ic) is obtained by dehydration condensation of the compound shown by the formula: Ar—COOH (wherein Ar has the same meaning as defined above and "—COOH" indicates a carboxyl group, hereinafter the same) and the compound shown by the formula (6) in the presence of a dehydrating agent.

As the dehydrating agent used, N,N-dicyclohexylcarbodiimide (DCC), 1-[3-(dimethylamino)propyl]-3-ethylcarbodiimide (WSC), 1,1-carbonyldiimidazole (CDI), N,N-disuccinimidyl carbonate (DSC), a Bop reagent (Aldrich, U.S.), 2-(1H-benzotriazol-1-yl)-1,1,3,3-tetramethyl-uronium hexafluorophosphate (HBTU), 2-(1H-benzotriazol-1-yl)-1,1,3,3-tetramethyl-uronium tetrafluoroborate (TBTU), bromotrispyrrolidinophosphonium hexafluorophosphate (PyBroP (registered trademark) Novabiochem, Germany), diphenyl phosphoric acid azido (DPPA), phosphorous oxychloride, phosphorus trichloride, triphenylphosphine/N-bromosuccinimide, and the like can be given.

The amount of the dehydrating agent used is usually 1 to 3 mols per one mol of the compound shown by the formula Ar—COOH.

In this instance, a base such as pyridine, 4-(N,N-dimethylamino)pyridine, triethylamine, diisopropylethylamine, and diazabicyclo[5.4.0]undec-7-ene (DBU) are preferably caused to be present in the reaction system. These bases may be used either individually or in combination of two or more.

The amount of the base used is usually 0.0001 to 1 mol per one mol of the compound shown by the formula Ar—COOH.

The reaction can be carried out in an appropriate solvent.

Any solvent inert to the reaction can be used without particular limitation. For example, ether solvents such as tetrahydrofuran, diethyl ether, diisopropyl ether, 1,3-dimethoxyethane, and 1,4-dioxane; amide solvents such as N,N-dimethylformamide, N,N-dimethylacetamide, 1,3-dimethylimidazolinone, and N-methylpyrrolidone; halogenated hydrocarbon solvents such as methylene chloride, chloroform, carbon tetrachloride, 1,2-dichloroethane, and chlorobenzene; aromatic hydrocarbon solvents such as benzene, toluene, and xylene; aliphatic hydrocarbon solvents such as pentane, hexane, and heptane; alicyclic hydrocarbon solvents such as cyclopentane and cyclohexane; acetonitrile; dimethylsulfoxide; and mixed solvents of two or more of these solvents can be given.

The amount of the solvent used is usually 0.1 to 1,000 g per 1 g of the compound shown by the formula Ar—COOH.

The reaction smoothly proceeds at a temperature in a range from −20° C. to the boiling point of the solvent used.

The reaction time is usually from several minutes to several hours, although the reaction time varies depending on the reaction scale.

(β) Method 2

The compound of the formula (Ic) of the present invention is obtained by producing the compound shown by the formula: Ar—CO-hal (wherein hal indicates a halogen atom) and reacting the resulting compound with the compound shown by the formula (6) in the presence of a base.

As the base used, organic bases such as triethylamine, diisopropylethylamine, pyridine, 4-(N,N-dimethylamino) pyridine, and diazabicyclo[5.4.0]undec-7-ene (DBU); inorganic bases such as sodium hydroxide, potassium hydroxide, magnesium hydroxide, sodium carbonate, potassium carbonate, sodium methoxide, sodium ethoxide, and potassium t-butoxide; and the like can be given. These bases may be used either individually or in combination of two or more.

The amount of the base used is usually 1 to 3 times mol per one mol of the compound shown by the formula Ar—CO-hal.

The reaction can be carried out in an appropriate solvent.

As the solvent, the same solvents mentioned above as the solvent used in the (a) method 1 can be given.

The reaction smoothly proceeds at a temperature in a range from −20° C. to the boiling point of the solvent used.

(γ) Method 3

The compound of the formula (Ic) of the present invention is also obtained by reacting the compound shown by the formula: Ar—COOH with an acid anhydride to obtain a mixed acid anhydride, and reacting the mixed acid anhydride with the compound shown by the formula (6).

There are no specific limitations to the acid anhydride used. As examples of the acid anhydride, acetic acid anhydride, trifluoroacetic acid anhydride, monochloroacetic acid anhydride, and the like can be given.

The amount of the acid anhydride used is usually 1 to 10 mols per one mol of the compound shown by the formula Ar—COOH.

The reaction can be carried out in an appropriate solvent.

Any solvent inert to the reaction can be used without particular limitation. For example, aromatic hydrocarbon solvents such as benzene, toluene, and xylene; aliphatic hydrocarbon solvents such as pentane, hexane, and heptane; alicyclic hydrocarbon solvents such as cyclopentane, cyclohexane, cyclooctane, and decaline; halogenated hydrocarbon solvents such as methylene chloride, chloroform, carbon tetrachloride, 1,2-dichloroethane, and chlorobenzene; ether solvents such as tetrahydrofuran, diethyl ether, diisopropyl ether, 1,3-dimethoxyethane, and 1,4-dioxane; amide solvents such as N,N-dimethylformamide, N,N-dimethylacetamide, 1,3-dimethylimidazolinone, and N-methylpyrrolidone; acetonitrile; dimethylsulfoxide; and mixed solvents of two or more of these solvents can be given.

The amount of the solvent used is usually 0.1 to 1,000 g per 1 g of the compound shown by the formula Ar—COOH.

The reaction proceeds smoothly at a temperature in a range from −20° C. to the boiling point of the solvent used.

(Manufacturing Method 2)

Among the liquid crystalline compounds of the present invention, the compound (Id) which is a compound having n=0 in the above formula (I) can be manufactured as follows:

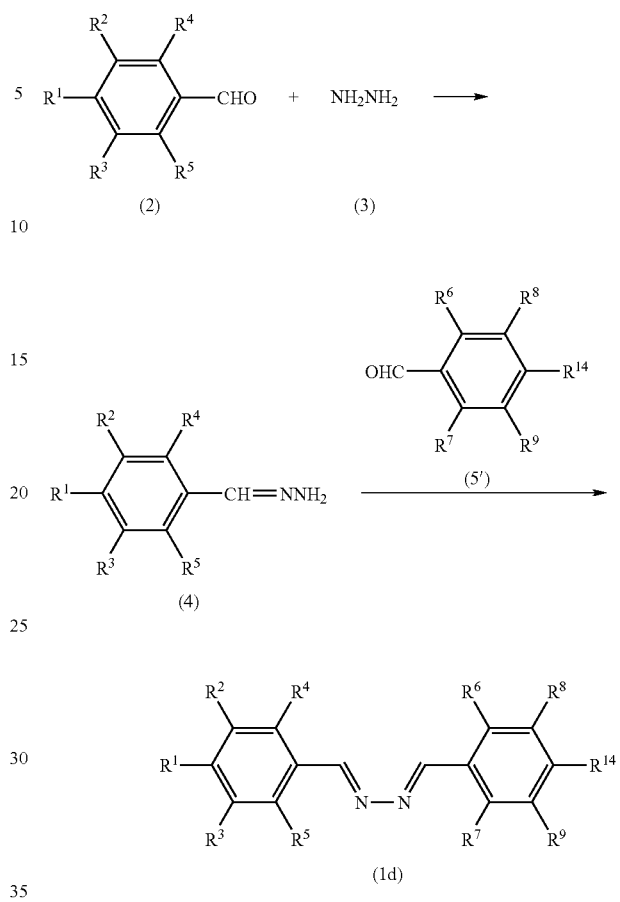

wherein $R^1$ to $R^9$ and $R^{14}$ have the same meanings as defined above.

Specifically, hydrazine (3) is reacted with a benzaldehyde compound shown by the formula (2) to obtain a hydrazone compound of the formula (4), which is reacted with a benzaldehyde compound of the formula (5') to obtain a compound shown by the formula (Id). The reactions can be carried out in the same manner as the reaction for obtaining the N,N'-hydrazone compound shown by the formula (6) from the benzaldehyde compound shown by the formula (2) in the above-mentioned manufacturing method 1.

(Manufacturing Method 3)

Among the liquid crystalline compounds of the present invention, the compound (Ie) which is a compound having n=0 and $R^{14}$=—O—CO—$CR^{15}$=$CH_2$ in the above formula (I) can be manufactured as follows:

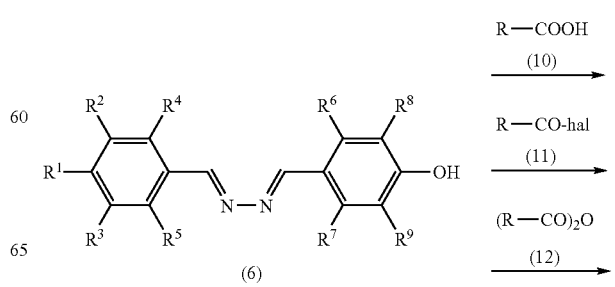

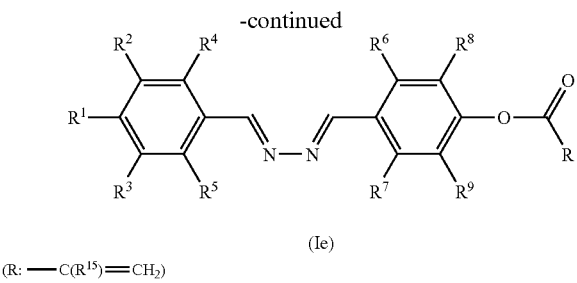

(Ie)

(R: —C(R¹⁵)=CH₂)

wherein R¹ to R⁹, hal, and R¹⁵ have the same meanings as defined above.

Specifically, the compound shown by the formula (Ie) can be obtained by reacting a carboxylic acid shown by the formula (10), an acid halide shown by the formula (11), or an acid anhydride shown by the formula (12) with the N,N'-hydrazone compound shown by the formula (6) which is obtained in the above manufacturing method 1. These reactions can be carried out in the same manner as the methods 1 to 3 in the above manufacturing method 1.

The carboxylic acids shown by the above formulas Ar—COOH and R—COOH, the acid halides shown by the above formulas Ar—CO-hal and R—CO-hal, and the acid anhydride shown by the above formula (R—CO)₂O are known compounds and can be prepared by general methods.

In any reactions, the reaction products may processed by a common post treatment method in organic chemistry after completion of the reaction and the target compounds can be isolated by a general purification and separation means such as column chromatography, recrystallization, distillation, and the like.

The structure of the target compound can be identified by measurement, elementary analysis, and the like using NMR spectrum, IR spectrum, mass spectrum, and the like.

2) Liquid Crystalline Composition

The liquid crystalline composition of the present invention (hereinafter referred to from time to time as "composition of the present invention") comprises one or more liquid crystalline compounds of the present invention (hereinafter referred to from time to time as "compound of the present invention").

Although not particularly limited, the proportion of the compound of the present invention in the composition of the present invention is usually 1 to 99 wt %, and preferably 5 to 60 wt % of the total amount of the composition.

The composition of the present invention preferably contains a polyfunctional (meth)acrylate compound having two or more groups shown by the formula —O—CO—CR¹⁶=CH₂, wherein R¹⁶ has the same meaning as defined above, in addition to the compound of the present invention.

The addition of the polyfunctional (meth)acrylate compound can further improve heat resistance and solvent resistance of the cured product of the composition of the present invention.

Any compounds having two or more groups shown by the formula —O—CO—CR¹⁶=CH₂ (hereinafter referred to as "(meth)acryloyloxy group") in the molecule and not detrimental to crystallinity and orientation of the liquid crystalline compound of the present invention can be used as the polyfunctional (meth)acrylate compound without particular limitation. Although such a polyfunctional (meth)acrylate compound may be either a liquid crystalline compound or a liquid non-crystalline compound, a liquid crystalline compound is preferable, with a compound (liquid crystalline compound) having as large as Δn which can produce a film having a large Δn being more preferable.

As such a (meth)acrylate compound, compounds shown by the following formula (14) are preferable.

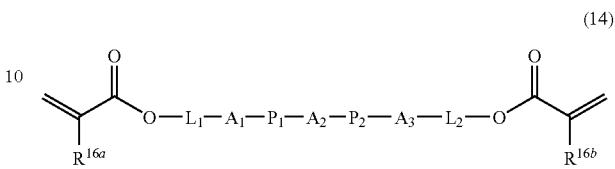

(14)

wherein $R^{16a}$ and $R^{16b}$ individually represent a hydrogen atom or a methyl group; $L_1$ indicates —$(CH_2)_d$— (wherein d is an integer of 0 to 10), —$(CH_2)_eO$— (wherein e is an integer of 1 to 10), or —$(CH_2CH_2O)_f$— (wherein f is an integer of 0 to 3); $L_2$ indicates —$(CH_2)_d$— (wherein d is an integer of 0 to 10), —$O(CH_2)_e$— (wherein e is an integer of 1 to 10), or —$(OCH_2CH_2)_f$— (wherein f is an integer of 0 to 3); $P_1$ and $P_2$ individually represent a —$CO_2$—, —O—, —OCO—, —CH=CH—, or a single bond; and $A_1$, $A_2$, and $A_3$ individually show a para-substituted cyclic group. Either —$CO_2$— or —OCO— has a carbonyl group.

The following groups are preferable as the para-substituted cyclic group shown by $A_1$, $A_2$, and $A_3$.

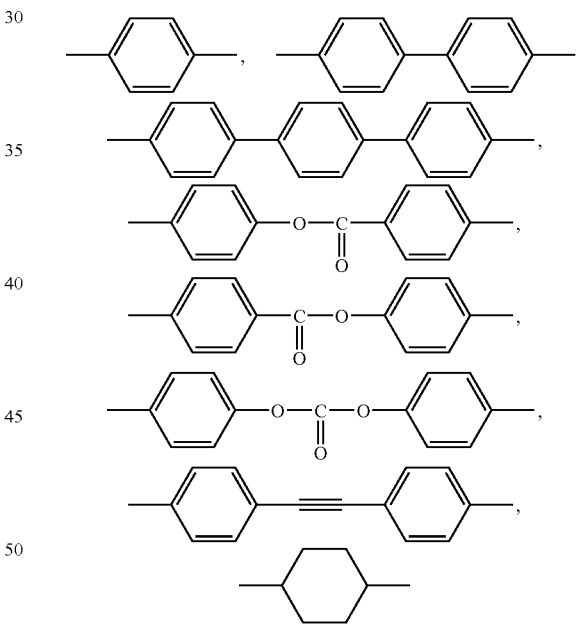

The hydrogen atoms on the para-substituted cyclic group may be substituted with an alkyl group having 1 to 6 carbon atoms such as a methyl group, an alkoxy group having 1 to 6 carbon atoms such as a methoxy group, or a halogen atom such as a fluorine atom.

As the liquid non-crystalline diacrylate compound having two or more (meth)acryloyloxy groups, a compound in which the (meth)acryloyloxy groups bond via an aliphatic hydrocarbon, a compound in which the (meth)acryloyloxy groups bond via an aromatic hydrocarbon, a compound in which the (meth)acryloyloxy groups bond directly or via an alkylene spacer from a polycyclic compound such as a compound described in JP-A-11-130729, and the like can be given.

As examples of the liquid non-crystalline compound having two (meth)acryloyloxy groups, compounds shown by the following formula (15) can be given.

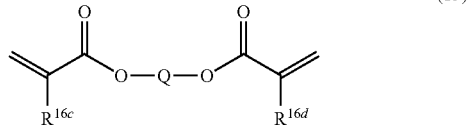

(15)

wherein Q is a linear or branched alkylene group having 2 to 12 carbon atoms, $R^{16c}$ and $R^{16d}$ individually represent a hydrogen atom or a methyl group.

As examples of the liquid non-crystalline compound having three (meth)acryloyloxy groups, compounds shown by the following formula (16) can be given.

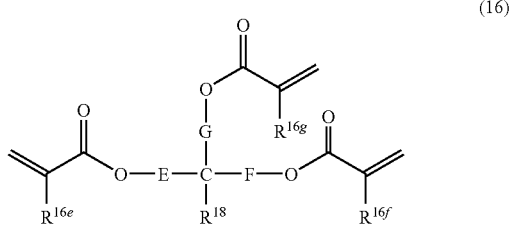

(16)

wherein E, F, and G individually represents —$(CH_2)_g$—, —$(CH_2)_h$—, or —$(CH_2)_i$— (wherein g, h, and i are integers of 0 to 10, provided that two or more of them are not 0 at the same time), $R^{16e}$, $R^{16f}$, and $R^{16g}$ individually represent a hydrogen atom or a methyl group, and $R^{18}$ represents a hydrogen atom or an alkyl group having 1 to 4 carbon atoms.

There are many liquid crystalline compounds and liquid non-crystalline compounds having two or more (meth)acryloyloxy groups known in the art other than the above compounds. Such other compounds may be used as the polyfunctional (meth)acrylate compounds for the liquid crystalline composition of the present invention.

Although not particularly limited, the polyfunctional (meth)acrylate comprising two or more (meth)acryloyloxy groups is used in an amount of preferably 10 to 1,000 parts by weight, and more preferably 100 to 800 parts by weight for 100 parts by weight of the liquid crystalline compound of the present invention.

As specific examples of the above-mentioned polyfunctional (meth)acrylate compounds, the compounds described in Published Japanese Translation of PCT Application 11-513360 (U.S. Pat. No. 5,833,880) and Published Japanese Translation of PCT Application 11-513019 (U.S. Pat. No. 6,136,225) can be given.

In addition to the liquid crystalline compound of the present invention and the polyfunctional (meth)acrylate compound, the composition of the present invention preferably contains a chiral compound. The composition can form a cholesteric liquid crystal layer due to inclusion of the chiral compound.

A generally known chiral compound may be used without particular limitation. For example, chiral compounds described in JP-A-2005-289881, JP-A-2004-115414, JP-A-2003-66214, JP-A-2003-313187, JP-A-2003-342219, JP-A-2000-290315, JP-A-6-072962, U.S. Pat. No. 6,468,444, and WO 98/00428 can be suitably used. Such a compound is commercially available as "Paliocolor LC756" manufactured by BASF, and "Chiracole CNL617R" or "Chiracole CNL-686L" manufactured by ADEKA.

The proportion of the liquid crystalline compound and the chiral compound in the composition of the present invention, in terms of the weight ratio, is 100:1 to 1:1.

In order to improve orientation and applicability to a substrate, various additives such as a leveling agent, a stabilizer, and a plasticizer may be added to the composition of the present invention, as required.

The types and amounts of other additives are generally known by a person skilled in the art, or may be determined through several preliminary experiments.

The amount of the other additives added is usually 0 to 10 wt % of the total amount of the composition.

The composition of the present invention may be prepared by dissolving the liquid crystalline compound of the present invention together with the poly(meth)acrylate compound and a chiral compound which are used as required, and the later-mentioned polymerization initiator, and optional additive in an appropriate solvent.

As specific examples of the solvent used, ketones such as cyclohexanone and methyl ethyl ketone, esters such as butyl acetate and amyl acetate, and halogenated hydrocarbons such as chloroform, dichloromethane, and dichloroethane can be given.

The composition of the present invention thus obtained is useful as a raw material for forming the optical film of the present invention and liquid crystal layers of the optical laminate of the present invention as described later.

3) Optical Film

The optical film of the present invention has a liquid crystal layer formed using the liquid crystalline composition of the present invention.

The optical film of the present invention may have any structure such as a structure in which the optical film is formed on an orientation substrate (orientation substrate/(alignment film)/optical film), a structure in which the optical film is transferred onto a transparent substrate film which differs from the orientation substrate (transparent substrate film/optical film), or a structure of an optical film single layer (optical film) when the optical film is self-supportable.

The optical film of the present invention can be prepared by (A) a method of applying a solution of the liquid crystalline composition of the present invention to an orientation substrate, drying the coated film, and subjecting the film to a heat treatment (orientation of liquid crystal) and an irradiation/heating treatment (polymerization) or (B) a method of applying a solution of the liquid crystalline polymer obtained by polymerizing the liquid crystalline composition of the present invention onto an orientation substrate.

When the composition of the present invention is polymerized in the above method (A) or (B), an initiator is added to the composition.

As the initiator, a radical polymerization initiator is preferable.

The radical polymerization initiator includes a heat-radical generating agent which initiates the radical polymerization by being heated and a photo-radical generating agent which initiates the radical polymerization by being irradiated.

The heat-radical generating agent include organic peroxides such as 1,1-bis(t-butylperoxy)-2-methylcyclohexane, 1,1-bis(t-hexylperoxy)-3,3,5-trimethylcyclohexane, 1,1-bis(t-hexylperoxy)cyclohexane, 1,1-bis(t-butylperoxy)-3,3,5-trimethylcyclohexane, 1,1-bis(t-butylperoxy)cyclohexane, 2,2-bis(4,4-di-butylperoxycyclohexyl)propane, 1,1-bis(t-butylperoxy)cyclododecane, t-hexylperoxyisopropylmonocarbonate, t-butylperoxymaleic acid, t-butylperoxy-3,5,5-trimethylhexanoate, t-butylperoxylaurate, 2,5-dimethyl-2,5-di (m-toluoylperoxy)hexane, t-butylperoxyisopropyl monocarbonate, t-butylperoxy-2-ethylhexyl monocarbonate, t-hexylperoxy benzoate, 2,5-dimethyl-2,5-di(benzoylperoxy)hexane, t-butylperoxy acetate, 2,2-bis(t-butylperoxy)butane, t-butylperoxy benzoate, n-butyl-4,4-bis(t-butylperoxy) valerate, di-t-butylperoxy-isophthalate, α,α-bis(t-butylperoxy)diisopropylbenzene, dicumylperoxide, 2,5-dimethyl-2,5-di(t-butylperoxy)hexane, t-butylcumylperoxide, di-t-butylperoxide, p-menthanehydroperoxide, 2,5-dimethyl-2,5-di(t-butylperoxy)hexin-3, diisopropylbenzenehydroperoxide, t-butyltrimethylsilylperoxide, 1,1,3,3-tetramethylbutylhydroperoxide, cumenehydroperoxide, t-hexylhydroperoxide, t-butylhydroperoxide, and benzoylperoxide; azo compounds such as azobisisobutyronitrile, 1,1-azobis(cyclohexane-1-carbonitrile), 2-(carbamoylazo)-isobutylonitrile, 2-phenylazo-4-methoxy-2,4-dimethylvaleronitrile, azo di-t-octane, azo di-t-butane, and 2,2'-azobis[N-(2-propenyl)-2-methylpropioneamide]; and the like.

The organic peroxide can also be used as a redox reaction agent by combining with a reducing agent.

Examples of the photo-radical generating agent include benzoins such as benzoin, benzoin methyl ether, and benzoin propyl ether; acetophenones such as acetophenone, 2,2-dimethoxy-2-phenylacetophenone, 2,2-diethoxy-2-phenylacetophenone, 1,1-dichloroacetophenone, 1-hydroxycyclohexyl phenyl ketone, 2-methyl-1-[4-(methylthio)phenyl]-2-morpholino-propan-1-one, and N,N-dimethylaminoacetophenone; anthraquinones such as 2-methylanthraquinone, 1-chloroanthraquinone, and 2-amylanthraquinone; thioxanethones such as 2,4-dimethylthioxanethone, 2,4-diethylthioxanthone, 2-chlorothioxanthone, and 2,4-diisopropylthioxanethone; ketals such as acetophenone dimethyl ketal and benzyl dimethyl ketal; benzophenones such as benzophenone, methyl benzophenone, 4,4-dichlorobenzophenone, 4,4-bisdiethylaminobenzophenone, Michiler's ketone, and 4-benzoyl-4-methyldiphenyl sulfide; and 2,4,6-trimethylbenzoyldiphenylphosphine oxide.

As specific examples of the photo-radical generating agent, Irgacure 907, Irgacure 184, Irgacure 369, Irgacure 651, and the like manufactured by Ciba Specialty Chemicals, Co. can be given.

These polymerization initiators may be used either individually or in combination of two or more.

As the orientation substrate used in the above methods (A) and (B), films of synthetic resins such as polyimide, polyamide, polyamideimide, polyphenylene sulfide, polyphenylene oxide, polyether ketone, polyether ether ketone, polyether sulfone, polysulfone, polyethylene terephthalate, polyethylenenaphthalate, polyallylate, triacetyl cellulose, epoxy resin, phenol resin, norbornene resin, and the like, as well as uniaxially alignment films produced from these synthetic resin films can be given.

A generally known method of providing a substrate with the orientational function may be employed without particular limitation. Specifically, a method of rubbing the surface of the substrate with a cloth or the like, a method of forming an organic thin film of polyimide, polyvinyl alcohol, or the like on the substrate surface and rubbing the organic thin film with a cloth, a method of forming an alignment film by oblique evaporation of $SiO_2$ onto the substrate, a method of irradiating an organic thin film having a functional group which is reactive by photo-dimerization in the molecule or an organic thin film having an optically isomerized functional group in the molecule with a polarizing light or a non-polarizing light, and the like can be given.

In order to provide a uniformly oriented state, a polyimide thin film which gives a pretilt angle used in a general twisted nematic element or supertwisted nematic element which can easily control the orientation state of liquid crystal molecules may be used.

In general, when a liquid crystalline composition is caused to come in contact with a substrate having an orientational function, liquid crystal molecules are oriented near the substrate in the direction along which the substrate has been treated for orientation. The direction in which the liquid crystal molecules orient (horizontal, oblique, or vertical) is largely affected by the method of orientation of the substrate.

For example, when an orientated film having a very small pretilt angle which is used for a liquid crystal display element of an in-plane switching (IPS) system is provided on a substrate, an almost horizontally orientated polymerizable liquid crystal layer is obtained.

When an alignment film which is used for a TN-type liquid crystal display element is provided on a substrate, a polymerizable liquid crystal layer with a slightly tilted orientation is obtained, whereas when an alignment film which is used for an STN-type liquid crystal display element is provided on a substrate, a polymerizable liquid crystal layer with a significantly oblique orientation is obtained.

When the composition of the present invention is caused to come in contact with a substrate having a horizontal orientational function with a pretilt angle, an optical anisotropic body which is obliquely oriented while uniformly or continuously changing the angle from near the substrate to near the air interface can be obtained.

If a method (optical orientation method) in which an organic thin film having a functional group which is reactive by a photo-dimerization reaction or an organic thin film having a functional group which is isomerized by radiation in the molecule (hereinafter abbreviated to "optically alignment film") is irradiated with polarizing light or non-polarizing light, a substrate having areas each with an orientation direction differing from the others distributed in a pattern form, can be obtained.

First, a substrate having an optically alignment film provided thereon is irradiated with a light of which the wavelength is within the absorption band of the optically alignment film to prepare a substrate on which a uniform orientation can be obtained. After that, the substrate is covered with a mask and irradiated with a light differing from the first irradiated light with an absorption wavelength of the optically alignment film, for example, a light with a different polarizing state or a light with a different irradiation angle and direction to provide the film with an orientational function differing from that of the area obtained by the first irradiation selectively on the irradiated area.

If the composition of the present invention is caused to come in contact with the substrate over which the regions in which the orientational function differs are distributed in a pattern form obtained by the method as mentioned above, the regions in which the orientation directions differ in a pattern form is distributed according to the orientational function of the substrate. A liquid crystalline polymer film with an orientation pattern can be obtained if radiation polymerization is carried out in this state.

When a substrate having an approximately horizontal orientational function in which the regions with different orientation directions are distributed in a pattern form is used as the above substrate, a liquid crystalline polymer film which is particularly useful as a phase difference film can be obtained.

In addition, as other methods of obtaining an oriented pattern, a method not using an optically alignment film such as a method of rubbing the alignment film with an AFM sensing pin, a method of etching an optical anisotropic body, and the like can also be given. The methods of using an optically alignment film are simple and preferred.

In the above method (A), the composition of the present invention is first coated onto the orientation substrate. Various generally known methods of application which ensure uniform coating may be employed without particular limitation. For example, a roll coating method, a die coating method, a dip coating method, a curtain coating method, a spin coating method, and the like can be given. A solvent removing (drying) step such as a method of using a heater or blowing hot air may be provided after the coating.

The coated film of the composition of the present invention is then dried, liquid crystals are aligned by heat treatment or the like as required, and the composition is polymerized (cured) to produce an optical film having a liquid crystal layer on the orientation substrate.

The heat treatment of the dried film of the composition of the present invention is a step of orienting the liquid crystal utilizing the self-orientation capability inherently possessed by the liquid crystalline composition by heating the composition in a liquid crystal phase producing temperature range. Such a heat treatment enables preparation of a uniform liquid crystalline polymer film with smaller orientation defects as compared with a method of simply coating the composition.

The optimum conditions and critical values vary according to the liquid crystal phase behavior temperature (transition temperature) of the liquid crystalline composition used. The temperature of the heat treatment is usually from 10 to 200° C., and preferably from 20 to 150° C.

The heat treatment time is usually 3 seconds to 30 minutes, and preferably 10 seconds to 10 minutes. Liquid crystals may not be sufficiently oriented if the heat treatment time is shorter than 3 seconds. A heat treatment time longer than 30 minutes unduly impair productivity. After completion of liquid crystal orientation by heat treatment or the like, the liquid crystalline composition on the orientation substrate is cured as is by the polymerization reaction.

After coating, it is preferable to cause the liquid crystal molecules in the composition to be uniformly oriented in a state in which the nematic phase is maintained. Specifically, the orientation can be promoted by heat treatment which accelerates the liquid crystal orientation.

The heat treatment is carried out as follows. Specifically, after coating the liquid crystalline composition of the present invention onto the substrate, the coating is heated to a temperature above the phase transition temperature of the nematic phase and the isotropic liquid phase (hereinafter abbreviated to "N-I transition temperature") of the composition to cause the liquid crystalline composition to take an isotropic liquid state. The liquid crystalline composition is then gradually cooled, as required, to cause the nematic phase to be exhibited. In this instance, it is preferable to maintain the composition at a temperature at which the liquid crystal phase is exhibited to cause the liquid crystal phase domain to grow sufficiently into a mono-domain.

After coating the liquid crystalline composition of the present invention onto the substrate, it is possible to heat the coated composition for a certain period of time at a temperature at which the nematic phase of the liquid crystalline composition is exhibited.

If the temperature is too high, the polymerizable liquid crystalline compound may be deteriorated due to undesirable polymerization reaction. If excessively cooled, the polymerizable liquid crystal composition may cause phase separation and deposit crystals to produce a high order liquid crystal phase like a smectic phase, making it impossible to effect an orientation treatment.

After such a uniform orientation, the coated film is cooled to the lowest temperature at which the liquid crystal phase does not cause phase separation, i.e. to excessively cooled conditions, and polymerized at that temperature while maintaining the liquid crystal phase to be oriented, whereby a liquid crystalline polymer film having a high orientation order and excellent transparency can be obtained.

When the composition of the present invention contains a heat radical generating agent, a liquid crystalline polymer film can be formed by heating the coated film of the composition of the present invention. The temperature at which the coated film of the composition is heated is preferably 40 to 250° C., and more preferably 50 to 200° C.

When the composition of the present invention contains a photo-radical generating agent, a liquid crystal layer can be formed by polymerizing the coated film of the composition of the present invention by irradiation. The latter is preferred in the present invention.

Although various methods can be used for polymerizing the resin composition of the present invention without specific limitations, a method of polymerizing the coated film by irradiation of light having a wavelength of 350 to 400 nm is preferable. Since the absorption end of ultraviolet radiation of the liquid crystalline compound is extended to near 350 nm, particularly when Δn of the polymerizable liquid crystalline compound is 0.18 or more, it is preferable to radiate only light with a wavelength of 350 to 400 nm which is absorbed only with difficulty by the polymerizable liquid crystalline compound. Efficient polymerization of the polymerizable liquid crystalline compound over the entire thickness direction of the coated film by a photo-polymerization initiator is initiated by irradiating light including light with a wavelength in this range, whereby a cholesteric liquid crystal layer which has a wide selective reflection zone of the polymerizable liquid crystalline compound can be formed.

The amount of ultraviolet-radiation required for the polymerization conversion rate of the polymerizable liquid crystalline compound to reach 100% varies according to the polymerizable liquid crystalline compound. The total dose of light with a wavelength of 350 to 400 nm is usually 200 to 1500 mJ/cm$^2$.

The radiation time of the light with a wavelength of 350 to 400 nm is preferably 0.1 to 10 seconds, more preferably 0.1 to 5 seconds, and still more preferably 0.1 to 3 seconds. The radiation time in the above range can promote productivity of the liquid crystalline polymer film.

In the above method (B), the liquid crystalline polymer is first obtained by polymerizing the composition of the present invention. Next, a solution of the resulting liquid crystalline polymer is prepared and an optical film is produced by a method of applying the solution onto an orientation substrate.

The polymerization of the composition of the present invention can be carried out in an appropriate organic solvent. Any inert solvents may be used without particular limitation. Examples include ketones such as cyclohexanone and methyl ethyl ketone, esters such as butyl acetate and amyl acetate, and halogenated hydrocarbons such as chloroform, dichloromethane, and dichloroethane. Among these, solvents having a boiling point of 60 to 250° C., particularly 60 to 150° C., are preferable from the viewpoint of ease of handling.

After the polymerization reaction, the target liquid crystalline polymer is isolated from the polymerization reaction solution.

The number average molecular weight of the liquid crystalline polymer is preferably from 2,000 to 500,000, and more preferably from 5,000 to 300,000. If the number average molecular weight is less than 2,000, the film may be damaged during the lamination step or the like due to lack of mechanical strength. If more than 500,000, the viscosity of the solution is large, resulting in a decrease of coatability. In addition, solubility of the polymer in a solvent may decrease.

The liquid crystalline polymer is thus obtained by polymerization of the liquid crystalline compound of the present invention which exhibits a high crosslinking efficiency due to crosslinking points uniformly distributed in the molecule. The polymer therefore has a high hardness.

It is preferable that the resulting liquid crystalline polymer have a pencil hardness according to JIS K 5600-5-4 of 2H or more. When used as an optical film or an optical laminate, the liquid crystalline polymer with a high hardness may be laminated with other functional materials onto a substrate such as glass without damaging the surface.

Next, the resulting liquid crystalline polymer is dissolved into an appropriate organic solvent to prepare a solution.

As the solvent used for dissolving the liquid crystalline polymer, ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; and ethers such as tetrahydrofuran, 1,2-dimethoxyethane, and 1,4-dioxane can be given.

Next, the solution is applied to a suitable supporting body to obtain a coated film. After drying, the coated material is heated into an isotropic liquid, which is gradually cooled to maintain the liquid crystal state.

A commonly known method can be used for coating the solution of the liquid crystalline polymer onto a supporting body. Examples include a curtain coating method, a knockout coating method, a roll coating method, a spin coating method, a dipping coating method, a bar coating method, a spray coating method, a slide coating method, a print coating method, and the like.

The optical film obtained by the above method (A) or method (B) is a sufficiently strong film. Specifically, mesogens are three-dimensionally bonded by the curing reaction to increase not only heat resistance (upper limit temperature of maintaining liquid crystal orientation), but also mechanical strength such as scratch resistance, wear preventing properties, and anticrack properties are significantly improved as compared with the film before curing.

The orientation structure of the film can be controlled by appropriately selecting the compound optionally added to the composition of the present invention. It is possible to produce optical films in which nematic orientation, torsion nematic orientation, cholesteric orientation, nematic hybrid orientation, and the like are fixed. The films are used for various applications according to the type of orientation.

Among these, optical films with the nematic orientation and torsion nematic orientation fixed therein, for example, function as a phase difference film and are used as a compensator of a transmissive or reflective liquid crystal display equipment of STN-type, TN-type, OCB-type, or HAN-type.

The film in which the nematic hybrid orientation is fixed can be used as a phase difference film or a wavelength plate utilizing retardation when viewed from the front or as a viewing angle improvement film of a TN-type liquid crystal display utilizing asymmetric properties according to the direction (inclination of the film) of a retardation value.

The optical film having a ¼ wavelength plate function can be used in combination with a polarizing plate as a reflection preventing filter of a reflection-type liquid crystal display used in EL display equipment.

An optical film in which the cholesteric orientation is fixed (selective reflection film) can be produced by polymerizing a liquid crystalline composition containing a chiral compound. The selective reflection film has a selective reflection wavelength zone in a part of a visible ray region. The selective reflection wavelength zone can be appropriately changed by adjusting the amount of the chiral compound used.

As the method for extending the selective reflection wavelength zone of a selective reflection film to the entire visible ray region, a method of laminating two or more selective reflection films produced by changing the amount of the chiral compound to be added and a method of coating the liquid crystalline composition solution having different selective reflection wavelength zones in layers on the resulting selective reflection film can be given.

The cholesteric polarizer can be obtained by laminating a phase difference film on a selective reflection film. As a phase difference film, a $\lambda/4$ plate is suitable. For example, a birefringence film obtained by stretching a polymer film and a liquid crystal orientation film having an optical anisotropic layer consisting of a liquid crystalline material are used. Although any generally known materials can be used without particular limitation as the material of the stretched film used as the $\lambda/4$ plate, polycarbonate, norbornene resin, polyvinyl alcohol, and the like are preferable.

The cholesteric polarizer can be prepared by a method of laminating a selective reflection film and a 214 plate, or a method of laminating a selective reflection film on a $\lambda/4$ plate with a liquid crystalline film secured thereon by coating and orienting the liquid crystalline composition.

In addition, it is possible to laminate two or more layers of such a liquid crystalline polymer film by a laminating method to obtain a multilayer polarizer which covers all the light of visible spectra by appropriately selecting the wavelength of the selected liquid crystalline polymer film (EP 0 720 041).

Instead of producing such a multilayer polarizer, the liquid crystalline polymer film may be used for fabricating a broadband polarizer by combining appropriate compounds and appropriate process conditions. The methods described in, for example, WO 98/08135, EP 0606940, GB 2312529, and WO 96/02016 may be used.

A color filter can be produced using the composition of the present invention. In order to produce a color filter, a necessary wavelength may be appropriately applied according to a coating method commonly used by a person having an ordinary skill in the art.

Moreover, thermochromism of cholesteric liquid crystals can also be used. The color of a cholesteric layer changes to blue via green from red by adjusting the temperature. A specific zone can be polymerized at a prescribed temperature using a mask.

In addition to the selective reflection film, the resulting optical film may be used as a phase difference film (optical compensation film), a torsion phase difference film, a tilted phase difference film, and the like.

The phase difference film can be obtained by forming a liquid crystalline composition to be oriented on an orientation film by heating. The torsion phase difference film can be obtained by adding a small amount of a chiral compound to the liquid crystalline composition. The torsion angle can be freely controlled by the amount of the chiral compound added. The tilted orientation phase difference film can be obtained by using an optically alignment film obtained by oblique irradiation of polarizing ultraviolet radiation as an alignment film. The angle of gradient can be controlled by the irradiation angle and dose of the polarized ultraviolet radiation.

4) Optical Laminate

The optical laminate of the present invention comprises a substrate, an alignment film formed on the substrate, and a liquid crystal layer formed on the alignment film using the liquid crystalline composition of the present invention.

As examples of the optical laminate of the present invention, a circular polarized light separation sheet, a retardation film, an orientation film for liquid crystal display elements, a polarizing plate, a viewing angle expansion board, a color filter, a low pass filter, an optical polarizing prism, and various light filters can be given.

EXAMPLES

The present invention will be described in more detail by way of examples and comparative examples. However, the present invention is not limited to these examples.

Example 1

Synthesis of Compound 1

A solution obtained by dissolving 3 parts by weight of 4-fluorobenzaldehyde in 50 parts by weight of ethanol was added to 10 parts by weight of hydrazine monohydrate, and the mixture was stirred for two hours at room temperature. 50 parts by weight of dichloromethane was added to the reaction mixture, and the resulting mixture was washed three times with 50 parts by weight of a saturated aqueous solution of sodium hydrogencarbonate. After the addition of 1 part by weight of triethylamine, the organic layer was dehydrated and dried using anhydrous sodium sulfate. The solvent was evaporated under reduced pressure. 1 part by weight of triethylamine was added, followed by the addition of 50 parts by weight of ethanol and 3 parts by weight of 4-hydroxybenzaldehyde. The mixture was stirred for eight hours at room temperature.

50 parts by weight of dichloromethane was added to the reaction mixture, the resulting mixture was washed three times with 50 parts by weight of a saturated aqueous solution of sodium hydrogencarbonate, and the solvent was evaporated under reduced pressure. The residue was purified by silica gel column chromatography to obtain 4.1 parts by weight of N-(4-fluorobenzylidene)-N'-(4-hydroxybenzylidene)hydrazine.

1 part by weight of N-(4-fluorobenzylidene)-N'-(4-hydroxybenzylidene)hydrazine, 1 part by weight of 4-(4-acryloxybutyl-1-oxy)benzoic acid, and 0.05 parts by weight of 4-(N,N-dimethylamino)pyridine (DMAP) were dissolved in 50 parts by weight of 1,4-dioxane. 1.5 parts by weight of dicyclohexylcarbodiimide (DCC) was added to the resulting solution while stirring. After stirring the entire amount at room temperature for 20 hours, the produced precipitate was removed by filtration and the solvent was evaporated under reduced pressure. The residue was purified by silica gel column chromatography to obtain 1.2 parts by weight of Compound 1. The yield was 42%.

$^1$H-NMR data of Compound 1 was as follows.

$^1$H-NMR (CDCl$_3$) δ ppm: 8.64 (d, 2H), 8.14 (d, 2H), 7.90 (d, 2H), 7.85 (d, 1H), 7.83 (d, 1H), 7.31 (d, 2H), 7.14 (t, 2H), 6.97 (d, 2H), 6.41 (dd, 1H), 6.12 (dd, 1H), 5.83 (dd, 1H), 4.25 (t, 2H), 4.09 (t, 2H), 1.91 (m, 4H)

The compound 1 obtained was phase transferred to the nematic phase at 108° C.

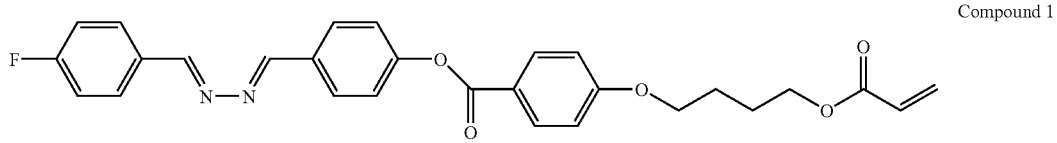 [SMILES: C=CC(=O)OCCCCOc1ccc(C(=O)Oc2ccc(/C=N/N=C/c3ccc(F)cc3)cc2)cc1]

Compound 1

Example 2

Synthesis of Compound 2

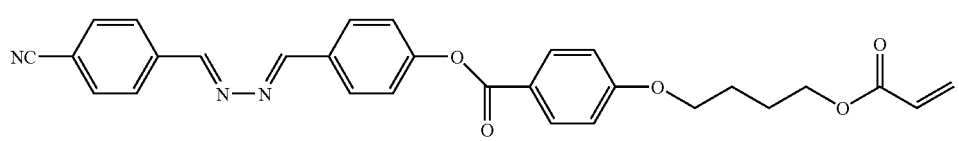

Compound 2

The target compound was obtained in the same manner as in Example 1, except that 4-cyanobenzaldehyde was used instead of 4-fluorobenzaldehyde. The yield was 51%.

$^1$H-NMR data of Compound 2 was as follows.

$^1$H-NMR (CDCl$_3$) δ ppm: 8.66 (d, 2H), 8.15 (d, 2H), 7.95 (d, 2H), 7.92 (d, 2H), 7.74 (d, 2H), 7.33 (d, 2H), 6.98 (d, 2H), 6.41 (dd, 1H), 6.13 (dd, 1H), 5.84 (dd, 1H), 4.26 (t, 2H), 4.10 (t, 2H), 1.92 (m, 4H)

Compound 2 obtained was phase transferred to the nematic phase at 130° C.

Example 3

Synthesis of Compound 3

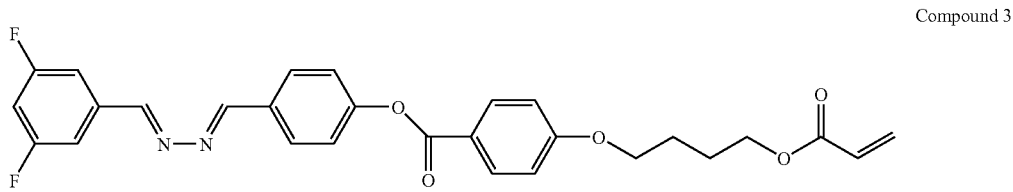 [SMILES: C=CC(=O)OCCCCOc1ccc(C(=O)Oc2ccc(/C=N/N=C/c3cc(F)cc(F)c3)cc2)cc1]

Compound 3

The target compound was obtained in the same manner as in Example 1, except that 3,5-difluorobenzaldehyde was used instead of 4-fluorobenzaldehyde. The yield was 49%.

$^1$H-NMR data of Compound 3 was as follows.

$^1$H-NMR (CDCl$_3$) δ ppm: 8.60 (d, 2H), 8.14 (d, 2H), 7.91 (d, 2H), 7.37 (m, 2H), 7.32 (d, 2H), 6.97 (d, 2H), 6.89 (m, 1H), 6.41 (dd, 1H), 6.13 (dd, 1H), 5.83 (dd, 1H), 4.26 (t, 2H), 4.09 (t, 2H), 1.92 (m, 4H)

Compound 3 obtained was phase transferred to the nematic phase at 123° C.

Example 4

Synthesis of Compound 4

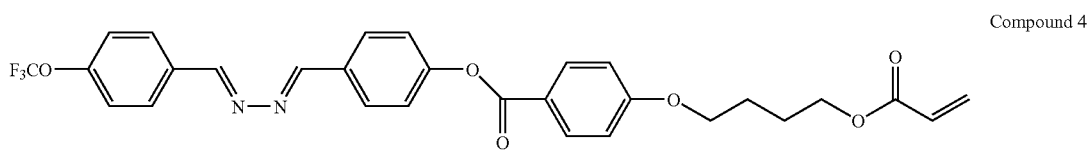 [SMILES: C=CC(=O)OCCCCOc1ccc(C(=O)Oc2ccc(/C=N/N=C/c3ccc(OC(F)(F)F)cc3)cc2)cc1]

Compound 4

The target compound was obtained in the same manner as in Example 1, except that 4-trifluoromethoxybenzaldehyde was used instead of 4-fluorobenzaldehyde. The yield was 55%.

$^1$H-NMR data of Compound 4 was as follows.

$^1$H-NMR (CDCl$_3$) δ ppm: 8.66 (d, 2H), 7.90 (t, 4H), 7.31 (t, 4H), 6.98 (d, 2H), 6.41 (dd, 1H), 6.13 (dd, 1H), 5.84 (dd, 1H), 4.26 (t, 2H), 4.10 (t, 2H), 1.93 (m, 4H)

Compound 4 obtained was phase transferred to the nematic phase at 109° C.

Example 5

Synthesis of Compound 5

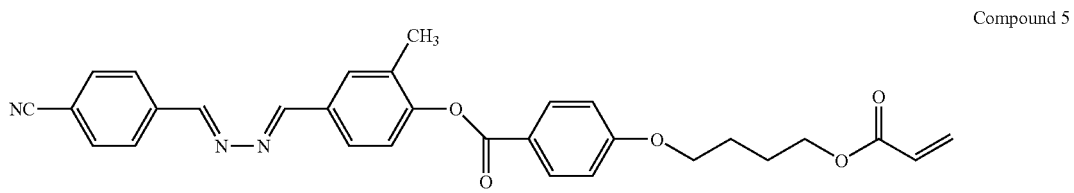

Compound 5

The target compound was obtained in the same manner as in Example 1, except that 4-cyanoaldehyde was used instead of 4-fluorobenzaldehyde and 3-methyl-4-hydroxybenzaldehyde was used instead of 4-hydroxybenzaldehyde. The yield was 32%.

$^1$H-NMR data of Compound 5 was as follows.

$^1$H-NMR (CDCl$_3$) δ ppm: 8.63 (d, 2H), 7.95 (d, 2H), 7.78 (s, 1H), 7.72 (d, 2H), 7.69 (d, 1H), 7.18 (d, 1H), 6.66 (dd, 1H), 6.37 (dd, 1H), 6.07 (dd, 1H), 2.26 (s, 3H)

Compound 5 obtained was phase transferred to the nematic phase at 149° C.

Example 6

Synthesis of Compound 6

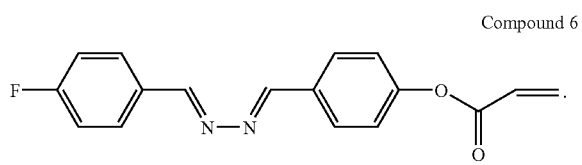 [SMILES: C=CC(=O)Oc1ccc(/C=N/N=C/c2ccc(F)cc2)cc1]

Compound 6

The target compound was obtained in the same manner as in Example 1, except that acrylic acid was used instead of 4-(4-acryloxybutyl-1-oxy)benzoic acid. The yield was 66%.

$^1$H-NMR data of Compound 6 was as follows.

$^1$H-NMR (CDCl$_3$) δ ppm: 8.62 (d, 2H), 7.88 (s, 1H), 7.85 (d, 1H), 7.83 (d, 1H), 7.81 (s, 1H), 7.23 (d, 2H), 7.13 (t, 2H), 6.62 (dd, 1H), 6.32 (dd, 1H), 6.03 (dd, 1H)

Compound 6 obtained was phase transferred to the nematic phase at 118° C.

Example 7

Synthesis of Compound 7

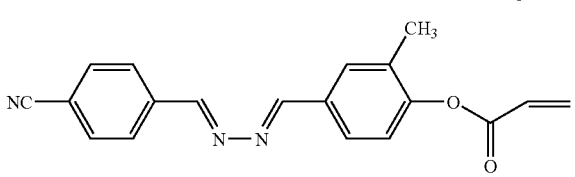

Compound 7

The target compound was obtained in the same manner as in Example 1, except that 4-cyanobenzaldehyde was used instead of 4-fluorobenzaldehyde, 3-methyl-4-hydroxybenzaldehyde was used instead of 4-hydroxybenzaldehyde, and acrylic acid was used instead of 4-(4-acryloxybutyl-1-oxy)benzoic acid. The yield was 43%.

$^1$H-NMR data of Compound 7 was as follows.

$^1$H-NMR (CDCl$_3$) δ ppm: 8.65 (d, 2H), 8.17 (d, 2H), 7.95 (d, 2H), 7.81 (s, 1H), 7.74 (d, 2H), 7.72 (d, 1H), 7.26 (d, 1H), 6.99 (d, 2H), 6.42 (dd, 1H), 6.13 (dd, 1H), 5.84 (dd, 1H), 4.26 (t, 2H), 4.11 (t, 2H), 2.30 (s, 3H), 1.92 (m, 4H)

The compound 7 obtained was phase transferred to the nematic phase at 128° C.

Examples 8 to 14

(1) Preparation of Transparent Resin Material Having Alignment Film

Both sides of an alicyclic olefin polymer film ("Zeonor film ZF14-100" manufactured by Optes, Inc.) were processed by corona discharge. One side of the film was coated with a 5% polyvinyl alcohol aqueous solution using a #2 wire bar. The coating was dried to form an orientation film with a thickness of 0.1 μm. The orientation film was rubbed to prepare a transparent resin substrate having an orientation film.

(2) Formation of Cholesteric Liquid Crystal Layer

The components shown in Table 1 were mixed at a ratio (wt %) shown in the Table to prepare cholesteric liquid crystalline compositions with a solid content of 40%. The cholesteric liquid crystalline compositions were coated on the orientation film side of the transparent substrates having the orientation film prepared in (1) above using a #8 wire bar. After orientation treatment at 75° C. for 5 minutes, the coated films on both sides were irradiated with UV light with a wavelength of 350 to 400 nm at a dose of 5 mJ/cm$^2$. After having been left in an oven at 100° C. for 3 minutes, the side with the coated film of the substrate was irradiated with a UV light with a wavelength of 350 to 400 nm at a dose of 200 mJ/cm$^2$ to cured the coating, thereby obtaining a cholesteric liquid crystalline film with a thickness of 4 μm having a cholesteric resin layer.

(3) Evaluation of Circular Polarization Separation Sheet

The transmission spectrum of the film prepared in (2) was measured using a spectrophotometer (moment multiphotometry system "MCPD-3000" manufactured by Otsuka Electronics Co., Ltd.) and a microscope (polarization microscope "ECLIPSE E600-POL" manufactured by Nikon Corp.). The central wavelength of selective reflection and the half-width of the selective reflection zone are shown in Table 1.

Comparative Example 1

A circular polarization separation sheet was prepared in the same manner as in Example 8 except for omitting the use of Compound 1. The central wavelength of selective reflection and the half-width of the selective reflection zone of the film were measured (Table 1, Comparative Example 1).

Comparative Example 2

A film was prepared in the same manner as in Example 8 except for using Compound 8 (shown below) which does not have a polymerizable group instead of Compound 1. The transmission spectrum could not be measured due to deposition of crystals (Table 1, Comparative Example 2).

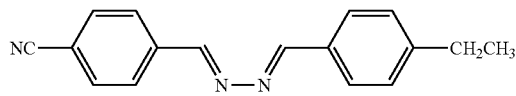

Compound 8

In Table 1, the following liquid crystalline compounds, chiral compound (chiral agent), polymerization initiator, surfactant, and solvent were used. The unit is parts by mass.

(1) Liquid crystalline compound: Poly-functional acrylate compound shown by the following formula ("LC242" manufactured by BASF)

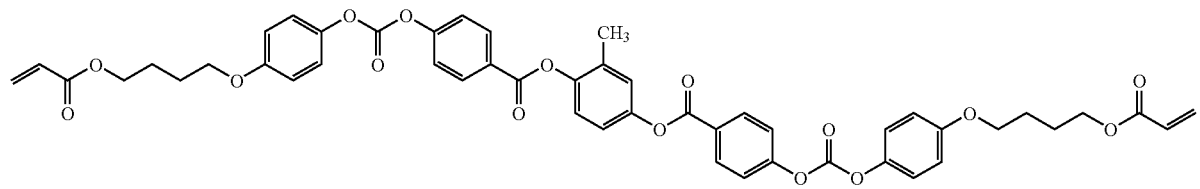 [SMILES: C=CC(=O)OCCCCOc1ccc(OC(=O)Oc2ccc(C(=O)Oc3ccc(OC(=O)c4ccc(OC(=O)Oc5ccc(OCCCCOC(=O)C=C)cc5)cc4)c(C)c3)cc2)cc1]

10

(2) Chiral agent: "LC756" manufactured by BASF
(3) Polymerization initiator: "IRGACURE379" manufactured by Ciba Specialty Chemicals Co.
(4) Surfactant: "KH40" manufactured by AGC SEIMI CHEMICAL CO., LTD.
(5) Solvent: Cyclopentanone

TABLE 1

|  | Example | | | | | | | Comparative Example | |
| --- | --- | --- | --- | --- | --- | --- | --- | --- | --- |
| Material | 8 | 9 | 10 | 11 | 12 | 13 | 14 | 1 | 2 |
| Liquid crystalline compound | 29.32 | 29.32 | 29.32 | 29.32 | 29.32 | 29.32 | 29.32 | 36.65 | 29.32 |
| Compound 1 | 7.33 | | | | | | | | |
| Compound 2 | | 7.33 | | | | | | | |
| Compound 3 | | | 7.33 | | | | | | |
| Compound 4 | | | | 7.33 | | | | | |
| Compound 5 | | | | | 7.33 | | | | |
| Compound 6 | | | | | | 7.33 | | | |
| Compound 7 | | | | | | | 7.33 | | |
| Compound 8 | | | | | | | | | 7.33 |
| Chiral agent | 2.11 | 2.11 | 2.11 | 2.11 | 2.11 | 2.11 | 2.11 | 2.11 | 2.11 |
| Polymerization initiator | 4.26 | 4.26 | 4.26 | 4.26 | 4.26 | 4.26 | 4.26 | 4.26 | 4.26 |
| Surfactant | 1.20 | 1.20 | 1.20 | 1.20 | 1.20 | 1.20 | 1.20 | 1.20 | 1.20 |
| Solvent | 55.78 | 55.78 | 55.78 | 55.78 | 55.78 | 55.78 | 55.78 | 55.78 | 55.78 |
| Selective reflection center wavelength (nm) | 660 | 650 | 630 | 640 | 640 | 640 | 630 | 515 | Crystals deposited |
| Reflection zone width (nm) | 95 | 90 | 85 | 90 | 90 | 90 | 90 | 50 | |

It can be seen from Table 1 that the cholesteric liquid crystal layers of Examples 8 to 14 formed from the liquid crystalline compositions containing Compound 1 to Compound 7 of Examples 1 to 7 exhibited a selective reflection center wavelength of 630 to 660 nm and showed a broad reflection zone width of 85 to 95 nm.

On the other hand, the cholesteric liquid crystal layer of Comparative Example 1 formed from the liquid crystalline composition not containing Compound 1 exhibited a selective reflection center wavelength of 515 nm and showed a narrow reflection zone width of 50 nm.

The liquid crystalline composition of Comparative Example 2 containing Compound 8 deposited crystals and could not form a uniform cholesteric liquid crystal layer.

INDUSTRIAL APPLICABILITY

The liquid crystalline compound and the liquid crystalline composition of the present invention are liquid crystalline materials having a high liquid crystal phase upper limit temperature, being chemically stable, manufactured at a low cost, and exhibiting a large selective reflection wavelength zone Δλ (that is, a large Δn).

The optical film and the optical laminate of the present invention having the liquid crystal layer formed using the liquid crystalline composition of the present invention are inexpensive and have a high quality.

The invention claimed is:
1. A liquid crystalline compound selected from the group consisting of compounds 1, 2, 3, 4, 5, 6 and 7 shown below:

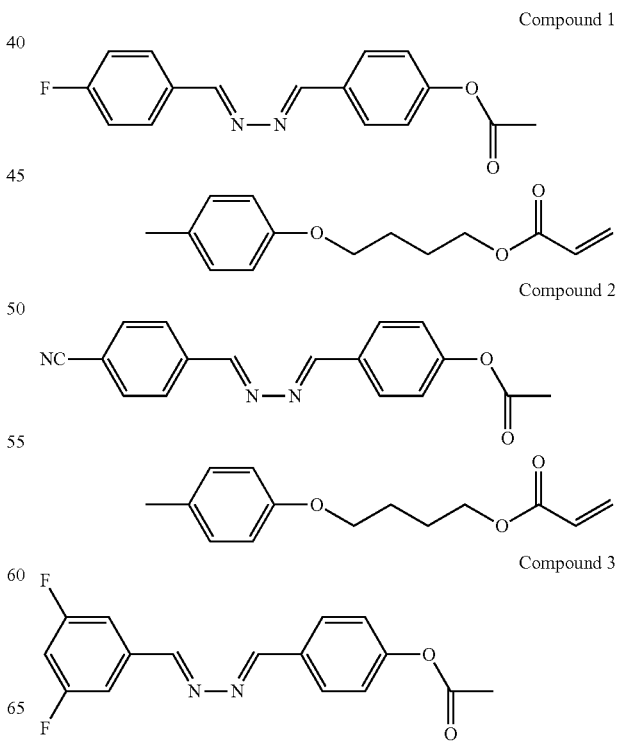

-continued

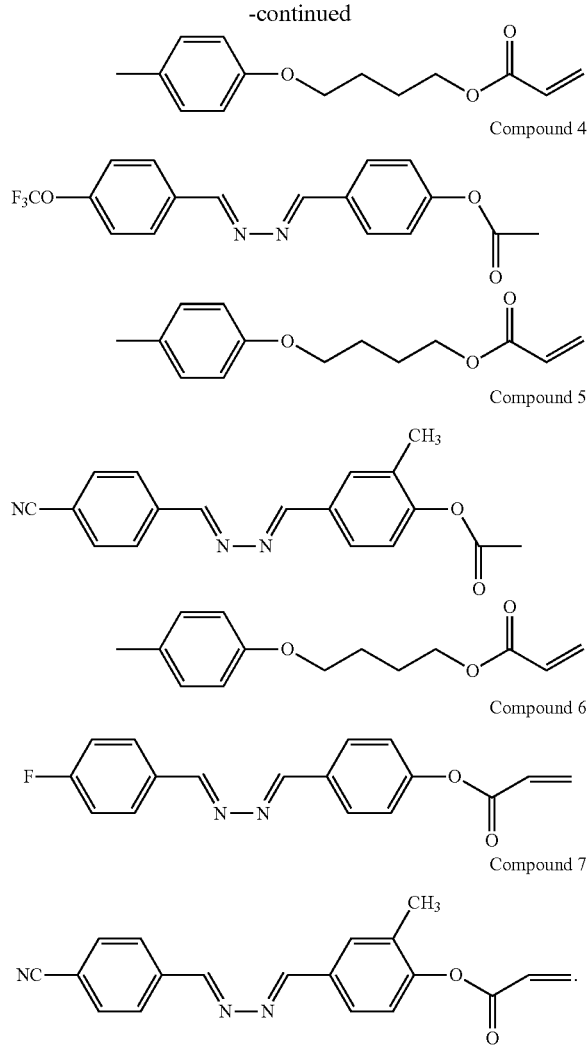

2. A liquid crystalline composition comprising one or more liquid crystalline compounds according to claim 1.

3. The liquid crystalline composition according to claim 2, further comprising a polyfunctional (meth)acrylate compound having two or more groups shown by the formula —O—CO—CR$^{16}$=CH$_2$, wherein R$^{16}$ represents a hydrogen atom or a methyl group, in the molecule.

4. The liquid crystalline composition according to claim 3, further comprising a chiral compound.

5. An optical film having a liquid crystal layer formed using the liquid crystalline composition according to claim 4.

6. An optical laminate comprising a substrate, an alignment film formed on the substrate, and a liquid crystal layer formed on the alignment film using the liquid crystalline composition according to claim 4.

7. The liquid crystalline composition according to claim 2, further comprising a chiral compound.

8. An optical film having a liquid crystal layer formed using the liquid crystalline composition according to claim 7.

9. An optical laminate comprising a substrate, an alignment film formed on the substrate, and a liquid crystal layer formed on the alignment film using the liquid crystalline composition according to claim 8.

10. An optical film having a liquid crystal layer formed using the liquid crystalline composition according to claim 2.

11. An optical film having a liquid crystal layer formed using the liquid crystalline composition according to claim 3.

12. An optical laminate comprising a substrate, an alignment film formed on the substrate, and a liquid crystal layer formed on the alignment film using the liquid crystalline composition according to claim 2.

13. An optical laminate comprising a substrate, an alignment film formed on the substrate, and a liquid crystal layer formed on the alignment film using the liquid crystalline composition according to claim 3.

* * * * *